US006885455B2

(12) United States Patent
Bartholomew et al.

(10) Patent No.: US 6,885,455 B2
(45) Date of Patent: Apr. 26, 2005

(54) SELF-CALIBRATION OF AN OPTICAL-BASED SENSOR USING A TOTAL INTERNAL REFLECTION (TIR) SIGNATURE

(76) Inventors: Dwight U. Bartholomew, 9615 Trailview Dr., Dallas, TX (US) 75238; Keren Deng, 5829 Cardigan Dr., Plano, TX (US) 75093

( * ) Notice: Subject to any disclaimer, the term of this patent is extended or adjusted under 35 U.S.C. 154(b) by 297 days.

(21) Appl. No.: 10/301,979

(22) Filed: Nov. 22, 2002

(65) Prior Publication Data

US 2004/0100634 A1 May 27, 2004

(51) Int. Cl.⁷ .............................................. G01N 21/55
(52) U.S. Cl. ....................................................... 356/445
(58) Field of Search ................................ 356/445, 446, 356/369

(56) References Cited

U.S. PATENT DOCUMENTS

| | | | | |
|---|---|---|---|---|
| 5,064,619 A | * | 11/1991 | Finlan | 356/445 |
| 5,313,264 A | * | 5/1994 | Ivarsson et al. | 356/445 |
| 5,822,073 A | * | 10/1998 | Yee et al. | 356/445 |
| 5,898,503 A | * | 4/1999 | Keller et al. | 356/445 |
| 5,912,456 A | | 6/1999 | Melendez et al. | |
| 5,917,608 A | * | 6/1999 | Naya et al. | 356/445 |
| 5,943,129 A | * | 8/1999 | Hoyt et al. | 356/318 |
| 5,946,083 A | * | 8/1999 | Melendez et al. | 356/73 |
| 6,045,756 A | * | 4/2000 | Carr et al. | 422/82.11 |
| 6,097,479 A | | 8/2000 | Melendez et al. | |
| 6,111,652 A | * | 8/2000 | Melendez et al. | 356/445 |
| 6,183,696 B1 | * | 2/2001 | Elkind et al. | 356/445 |
| 6,191,847 B1 | * | 2/2001 | Melendez et al. | 356/73 |
| 6,415,235 B1 | * | 7/2002 | Bartholomew et al. | 356/445 |
| 6,424,418 B2 | * | 7/2002 | Kawabata et al. | 356/445 |
| 6,462,809 B1 | * | 10/2002 | Ryan et al. | 356/128 |
| 6,798,521 B2 | * | 9/2004 | Elkind et al. | 356/445 |

* cited by examiner

Primary Examiner—Michael P. Stafira
Assistant Examiner—Juan D Valentin, II
(74) Attorney, Agent, or Firm—William B. Kempler; W. James Brady, III; Frederick J. Telecky, Jr.

(57) ABSTRACT

A surface plasmon resonance sensor or critical angle sensor has a reflecting surface which is optically flat and exposed to air on one side. Light reflecting from a sensing surface of the sensor which impinges on the reflecting surface at an angle which is less than the critical angle passes into the air whereas light which impinges at an angle which is equal to or greater than the critical angle is reflected onto a photodetector. The critical angle reflection from the reflecting surface provides a total internal reflection (TIR) characteristic which is used to calibrate the sensor.

20 Claims, 4 Drawing Sheets

SELF-CALIBRATION OF AN OPTICAL-BASED SENSOR USING A TOTAL INTERNAL REFLECTION (TIR) SIGNATURE

FIELD OF THE INVENTION

The present invention relates to self-calibration of an optical-based sensor and more specifically to self-calibration of a surface plasmon resonance sensor or a critical angle sensor.

BACKGROUND OF THE INVENTION

Surface plasmon resonance sensors which are integrally formed are known, for example, from U.S. Pat. No. 5,912,456, which is incorporated herein by reference. A surface plasmon resonance device can be utilized for sensing because of the oscillation of a surface-plasma of free electrons which exist at a conductor-dielectric boundary and which is affected by the refractive index of material adjacent to the conductor film surface which can be detected from the other side of the surface plasmon sensor. For a given wavelength of radiation, when the angle of incidence of polarized radiation has a particular value, which is dependent upon the refractive index of the material adjacent to film, resonance occurs. Changes in the refractive index of the material causes changes in the angle at which surface plasmon resonance occurs. When polarized light strikes the thin metal film at the resonance angle, the intensity of the reflected light is minimized. The sensor works by detecting the angle at which this minimum reflections occurs, and determining therefrom the refractive index of the material adjacent to the film. This patent shows an integrally formed surface plasmon resonance sensor. The sensor shown in FIG. 2 of the patent is similar to the sensor depicted FIG. 1 of the present application except that the light in FIG. 1 is reflected off of the sample first and then off of the mirror, which is the opposite of what is shown in the patent. This reversal of elements is specifically contemplated by the patent.

This integrally formed surface plasmon sensor is shown in FIG. 1 generally as 100. The sensor comprises an integrally formed housing 102 which is made of a material which is transparent to the radiation from the light source 104. As shown, the shape of the housing 102 is generally a trapezoidal shape, although the surfaces at the top 108 and bottom 140 thereof are not necessarily parallel. Light emitted from light source 104 as 112 impinges upon a sensing surface 106 which has a surface plasmon resonance element thereon. The surface plasmon resonance element may be a thin film of copper, silver or gold having a substantially uniform thickness. The material can be applied directly to the sensing surface or can be applied to a thin glass sheet which is then attached to the sensor. The light 114 which is deflected off of the surface plasmon sensor at 106 is reflected off of a mirror 108 onto a photodetector 110. The mirror is typically a gold film on a thin glass sheet which is attached to the top of the housing 102. The photodetector 110 is typically a line sensor having N×1 pixels, where N is the number of pixels along a single horizontal line in the photodetector. As described in the patent, it is common for the light source and photodetector to be mounted on a circuit board (not shown) which is then integrally formed such as by encapsulation, within the sensor 100. Although modern manufacturing techniques can place these components on the circuit board with high accuracy, it is possible to have a tolerance of ±4 mils for a component shift, which is equivalent to ±2 pixels on the photodetector 110. In order to achieve accurate results, it is necessary to calibrate the sensor. This calibration is typically performed by placing a liquid of known refractive index, such as water, on the surface plasmon sensor 106. The light source is activated and the resulting output of the photodetector is shown as signal 120. This signal has a minimum point 122, which represents the angle at which plasmon resonance occurs. As can be seen from FIG. 1, the shape of curve 120 is the reverse of the shape of curve 124, which is the characteristic of water, due to the reflection in mirror 108. The position of a minimum point is determined and compared to the expected minimum point. As shown in FIG. 2, curves representing the response of the sensor to a liquid on the sensing surface 106 are shown generally as 200. The curve 202 is the theoretical curve for the sensor response, if the components were precisely placed. The horizontal translation along the pixel position as shown in FIG. 1 results in the horizontal translation of the curve 202 without changing the shape thereof. Thus, the curve may vary between curves 206 and 208, for example, in response to the movement of the reflection minimum point. Once the appropriate curve is determined, the response of the sensor can be calibrated by changing the parameters of the equation which define the curve 202. The need to place a liquid upon the sensing surface 106, is undesirable and a disadvantage of this technique.

Critical angle sensors are known, for example, from the U.S. Pat. No. 6,097,479, which is incorporated herein by reference. This type of sensor utilizes the measurement of the critical angle to determine the refractive index of a material. The critical angle is a function of the refractive index. Light impinging upon the material at an angle which is equal to or exceeds the critical angle will undergo total internal reflection which occurs when light rays are incident from a medium having a high index of refraction onto the medium having a lower index of refraction. The transition from transmission to total internal reflection is utilized to measure the critical angle and to calculate the refractive index therefrom. FIG. 3 of present application is similar to the FIG. 3 of the patent, with two exceptions. The first is that in the patent light impinges upon the mirror 119 before impinging upon the sample whereas in the present application, the light is shown impinging upon the sample first and then the mirror second. Secondly, the configuration of the sensor of the patent has been modified in FIG. 3 and it is similar to the configuration shown in FIG. 1.

In FIG. 3 the critical angle sensor is shown generally as 300. The sensor is enclosed in housing 302 which is generally of the same shape as the housing 102 shown in FIG. 1. It contains a light source 304 which generates light 312 which impinges upon a sample on a sensing surface 306. The surface 306 is different from the surface 106 in FIG. 1 because there is no surface plasmon resonance element thereon. A glass plate may be attached to the housing at this point, to provide a flat surface for the sample. Space between the glass plate and the housing is filled with material having the same index of refraction as the housing. The light 312 impinges upon the surface 306 will therefore enter into the sample 318 and be reflected by the difference in the index of refraction between the housing 302 and sample 318, here shown as water. The light produced by this reflection 314 impinges upon a mirror 308 at the top of the housing 302. As in FIG. 1, the mirror 308 may be a glass plate having a gold film thereon attached to the top of the housing 302. The light that impinges upon the mirror 308 is reflected as 316 and impinges upon the photodetector 110. The characteristic for water 324 will appear across the elements of photodetector 310, except that they will be reversed, because of the reflection in the mirror 308. The curve 320 shows the output of the photodetector with respect to pixel position. As can be seen, there is a minimum point 322 which is the characteristic for water and which can be utilized to calibrate the position of the characteristic curve for the sensor. Sensors of this type are of similar construction to the sensors shown in FIG. 1 and thus suffer from this same problem with respect to tolerances in the assembly of the part. The tolerances are also present in the horizontal plane and a curve fitting technique as shown in FIG. 2 can be utilized to calibrates sensors of this type as well. As with the sensor in FIG. 1, these sensors will suffer from the disadvantage of having to place a liquid upon the sensor in order for the sensor to be calibrated.

SUMMARY OF THE INVENTION

It is a general object of the invention to provide a surface plasmon resonance sensor or critical angle sensor which has a self calibration standard.

This and other object and features are found in one aspect of the invention having a surface plasmon resonance sensor or critical angle sensor which has a housing containing a light source and a photodetector. The housing has a sensing surface having altered optical properties when in contact with a sample and a reflecting surface for directing light within the housing so that light from the light source is reflected by the sensing surface and the reflecting surface onto the photodetector. A self contained calibration standard in the housing in which the reflector surface is an optically flat surface on the housing having no reflective material thereon and having an outside of the flat surface exposed to air. The housing is made of a light transmissive material for light from the light source and has a higher index of refraction than air. Light impinging on the flat surface having an angle of incidence which is equal to or greater than a critical angle is reflected to a path which impinges onto the photodetector, whereby a characteristic response is detected by the photodetector which is indicative of a calibration point.

Another aspect of the invention includes a surface plasmon sensor or critical angle sensor includes a light transmissive housing having a higher index of refraction than air. A light source and a photodetector are disposed within the housing. A sensing surface is formed on one side of the housing. A reflecting surface is formed on another side of the housing having an exterior of the surface exposed to air. The light source, photodetector, sensing surface and reflecting surface are disposed in a light path wherein light emitted by the light source which impinges on the reflecting surface at an angle equal to or greater than a critical angle is reflected by the reflecting surface to a path in which it impinges on the photodetector. Light emitted by the light source which impinges on the reflecting surface at an angle less than the critical angle is refracted into the air, whereby the air-backed reflector surface generates a total internal reflection signature for calibrating the sensor.

Another aspect of the invention includes a method of calibrating a surface plasmon sensor or critical angle sensor having a light source, sensing surface, reflecting surface an exterior of which is exposed to air, and a photodetector enclosed in a light transmissive housing. Exciting the light source. Detecting a signal generated in the photodetector by light from the light source. Finding a characteristic signature in the signal generated by the photodetector which is generated by total internal reflection at the reflecting surface. Calibrating the sensor response by utilizing the location of the characteristic signature on the photodetector.

DETAILED DESCRIPTION OF THE PRESENT INVENTION

Figure 4:
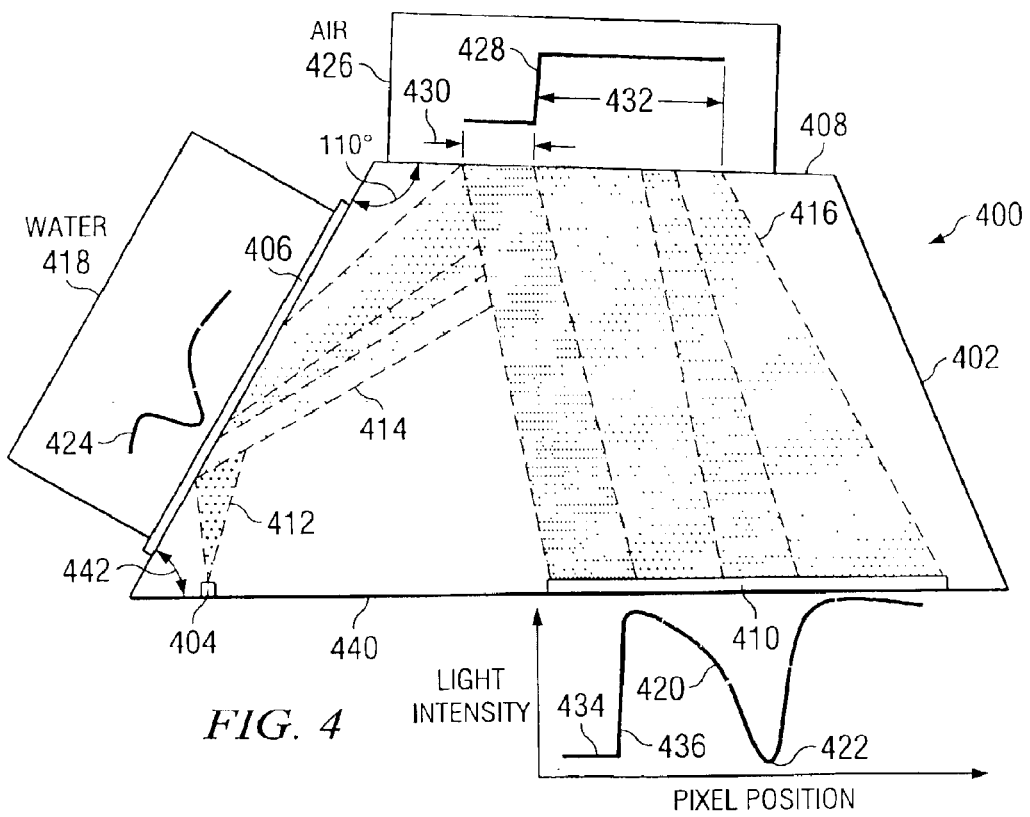
FIG. 4 shows the calibration technique for a surface plasmon resonance sensors utilizing the principles of the present invention.

A first embodiment of the present invention is shown in FIG. 4 in which a surface plasmon resonance sensor is generally shown as 400. The surface plasmon sensor 400 generally has a trapezoidal shaped body except that the top surface 408 and the bottom surface 440 need not be parallel. Advantageously, the body 408 is integrally formed with the other elements of the sensor in a molded housing as described in U.S. Pat. No. 5,912,456. Within the housing 402, a light source 404 located along the bottom 440 projects light 412 onto sensing surface 406. The surface 406 contains a surface plasmon resonance sensor thereon which may take the form of a metallic foil on a glass wafer or a metallic foil formed directly on a polished surface of the housing 402. The angle between sensing surface 406 and the top surface 408 is 110 degrees in this embodiment. The surface 408 does not have a mirror thereon, as found in the prior art. The inventors of the present invention have discovered that by omitting this part, a total internal reflection (TIR) signature can be achieved which can be used for calibration. Thus, the present invention provides self calibration while achieving a lower cost part. The surface 408 is exposed to air. As shown by the characteristic 428 for air, radiation 414 reflected from the sensing surface 406 will impinge upon top surface 408 at various angles. That portion 430 which impinges upon the surface 408 at less than the critical angle, will pass through the surface 408 into the air and be lost. That portion which impinges upon area 432 impinges at an angle equal to or greater than the critical angle, which causes total internal reflection. That light will therefore be reflected as 416 onto the photodetector 410 located on the bottom 440 of the body 402. It should be noted that for the portion 430, a very small percentage, perhaps 3%, of the light will be reflected onto the photodetector 410.

Figure 5:
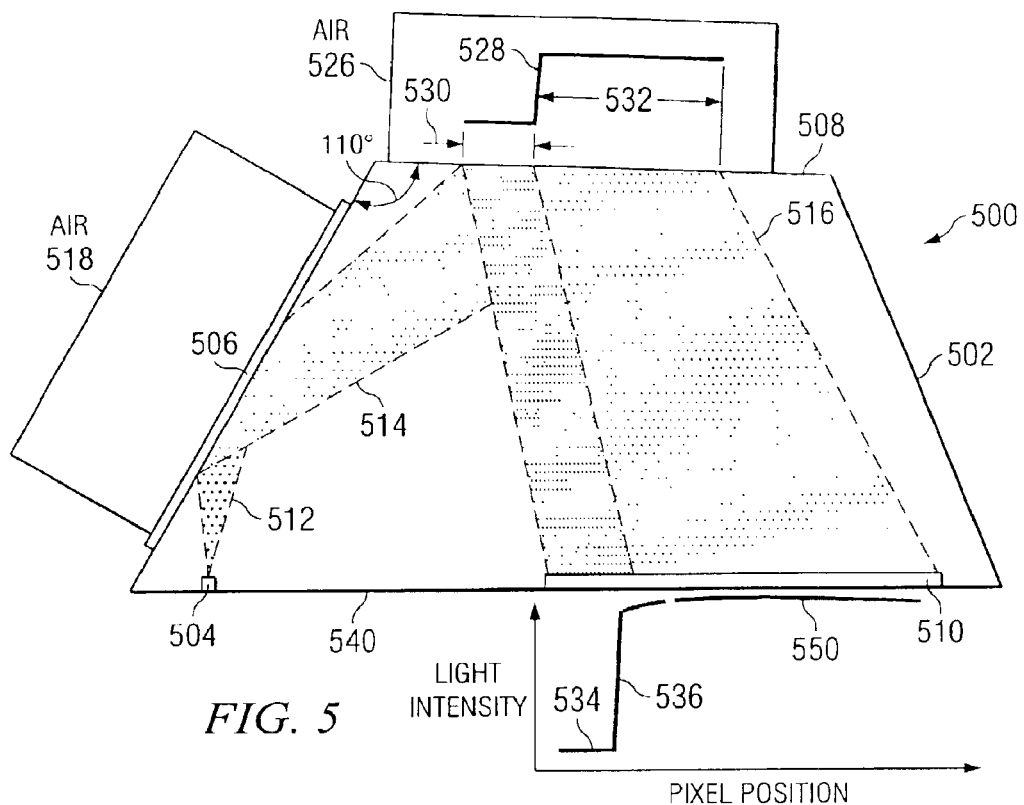
FIG. 5 shows the calibration technique of FIG. 4 without water present on the sensing surface.

As shown in FIG. 4, water 418 is present on the sensing surface 406. The characteristic for water 424 is reflected by the surface 408 to produce a reverse pattern along the photodetector 410. Underneath the figure, there is a graph showing the light intensity along the photodetector 410 with pixel position along the photodetector 410. As can be seen from the graph, the signal 420 starts out as essentially at zero or close to zero, level 434, followed by a sharply rising edge 436 followed by the pattern 424 for water (reversed due to the reflection from surface 408). The characteristic for water has a minimum point 422, at which the surface plasmon resonance will produce a dark area. This is used to detect the presence of water or other fluid on the sensing surface 406. If the water is not present on surface 406, and surface 406 is exposed to air, the light intensity across the photodetector 410 is composed of segments 434, 436 and a horizontal segment. This is shown in FIG. 5 in which all of the elements except 518 are identical to FIG. 4. Element 518 is air whereas element 418 is water. As can be seen from the graph, the TIR signature of air 534, 536 which corresponds to the segments 434, 436 is still present. The segment 550 is essentially horizontal because of the absence of the pattern for water. Therefore, this characteristic TIR signature of air can be utilized to calibrate the sensor without the need to place a liquid upon the sensing surface 406. It should be noted that the characteristic for air does not affect the sensing surface 406 because of the presence of the surface plasmon resonance sensors thereon.

Figure 6:
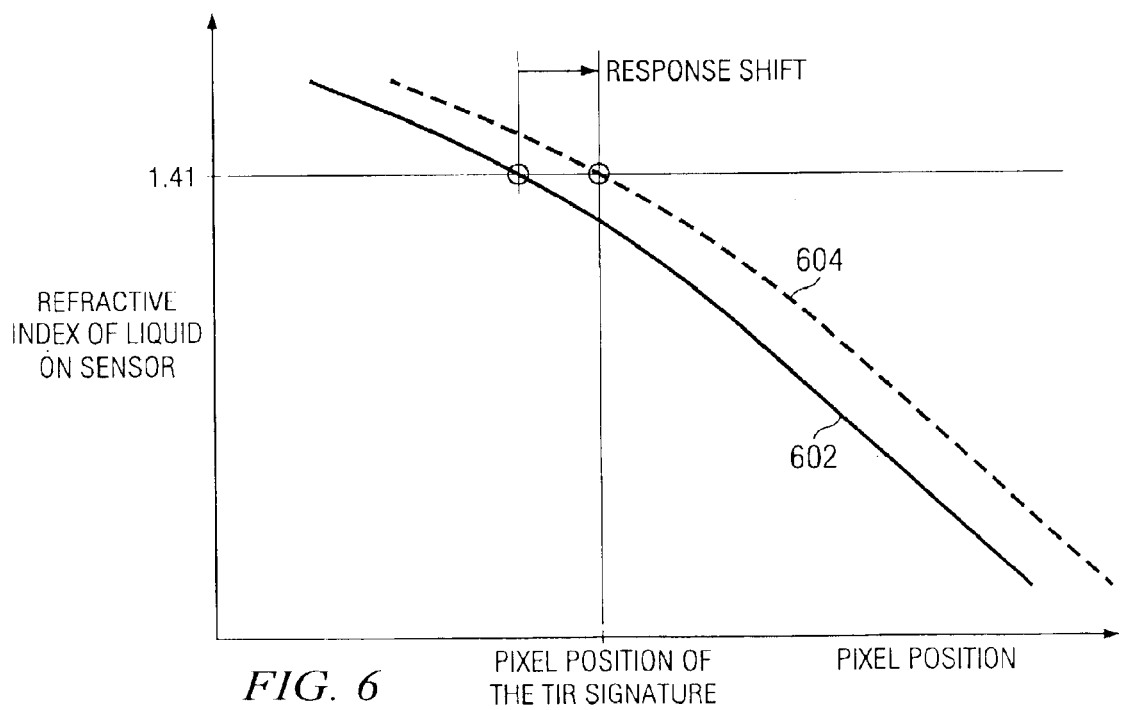
FIG. 6 illustrates the calibration of the sensor by shifting the response curve.

Referring to FIG. 6, curve 602 represents the response curve of the output of the photodetector 410 as a function of the refractive index of the liquid on the sensor vs. pixel position.

Figure 1:
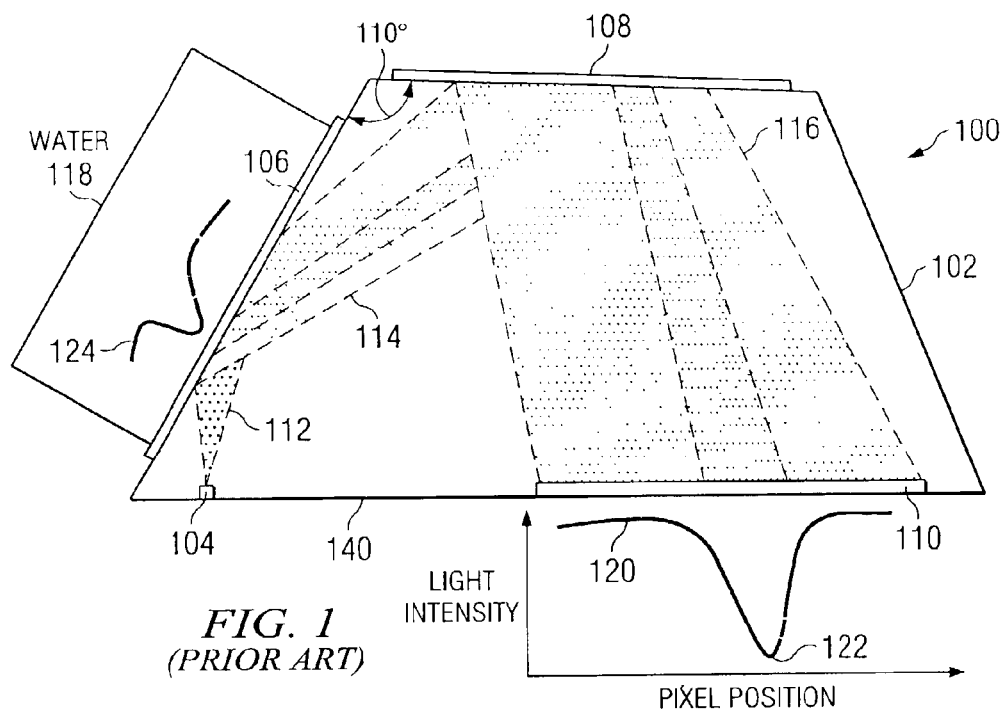
FIG. 1 shows a side view of a conventional calibration technique for calibrating a surface plasmon sensor.
Figure 2:
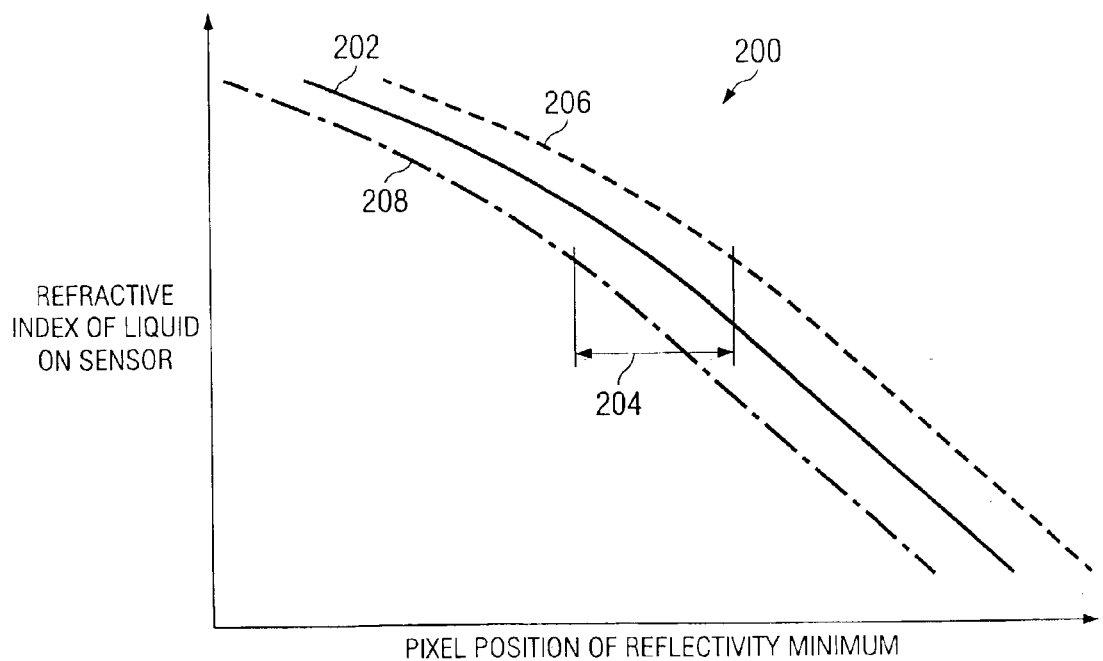
FIG. 2 shows a calibration of the response curve of the sensor of FIG. 1.

For the geometry shown and a polycarbonate plastic body 402, we expect the total internal reflection angle for air to be 40 degrees which is equivalent to an angle of 110 degrees, minus 40 degrees equals 70 degrees on the sensing surface 406. The expression for surface plasmon resonance tells us that, for polycarbonate, an angle of 70 degrees is equivalent of a liquid with a refractive index of 1.41. A refractive index of 1.41 is plotted on FIG. 6. Where this horizontal line intersects the curve 602, is the pixel position at which the TIR signature comprising elements 534, 536 and 550 should appear. However, as shown in FIG. 6, the actual pixel position is shifted to the right. Therefore, curve 604, shown as a dotted line in FIG. 6 and having the same shape as the curve 602, is the curve which represents the calibrated response from the photodetector 410. The curve is only translated horizontally, as shown in FIG. 2 because the errors due to the placement of the components only moved the characteristic position along the horizontal axis, and does not change the general shape of the curve. The calibration to the curve 604 can accomplished by changing some of the parameters in the equation that defines the shape of the curve 604 in order to represent the horizontal translation from the curve 602. Alternatively, points along the curve can be stored a look up table and the addresses of the table can be shifted to accommodate the translation of the curves.

The angle 442 between the sensing surface 406 and bottom 440 may be 68 degrees, for example, utilizing a gold film as a thin metal film on the surface plasmon resonance sensor which is attached to surface 406 and where water or a water solution is to be detected.

Figure 3:
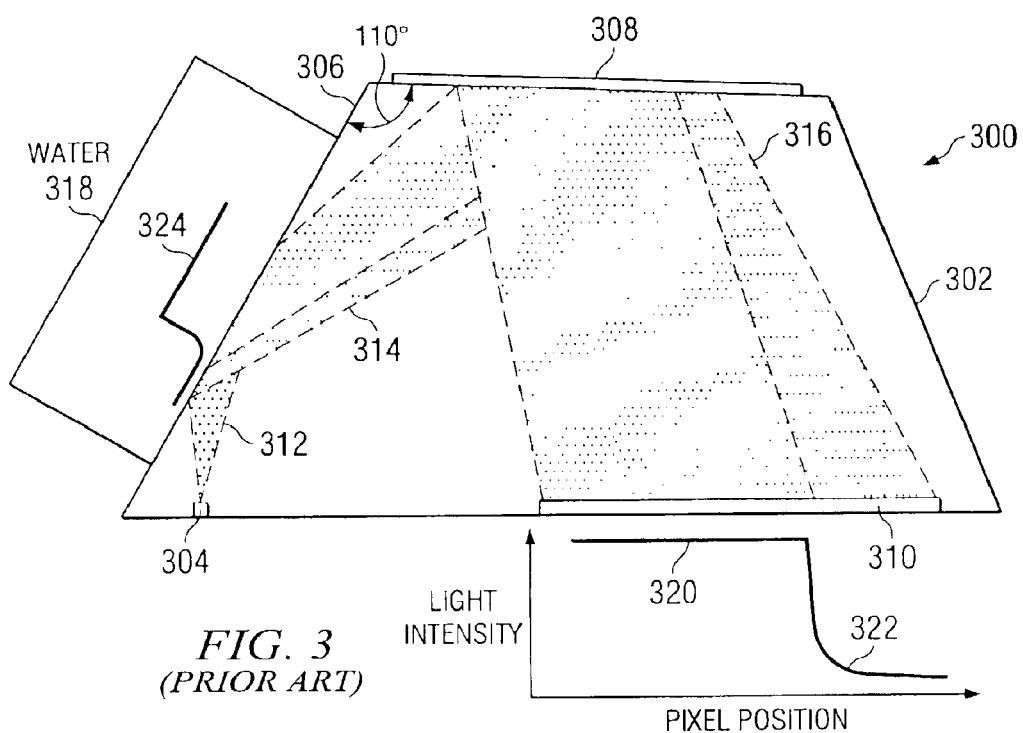
FIG. 3 shows a conventional calibration technique for a critical angle sensor.
Figure 7:
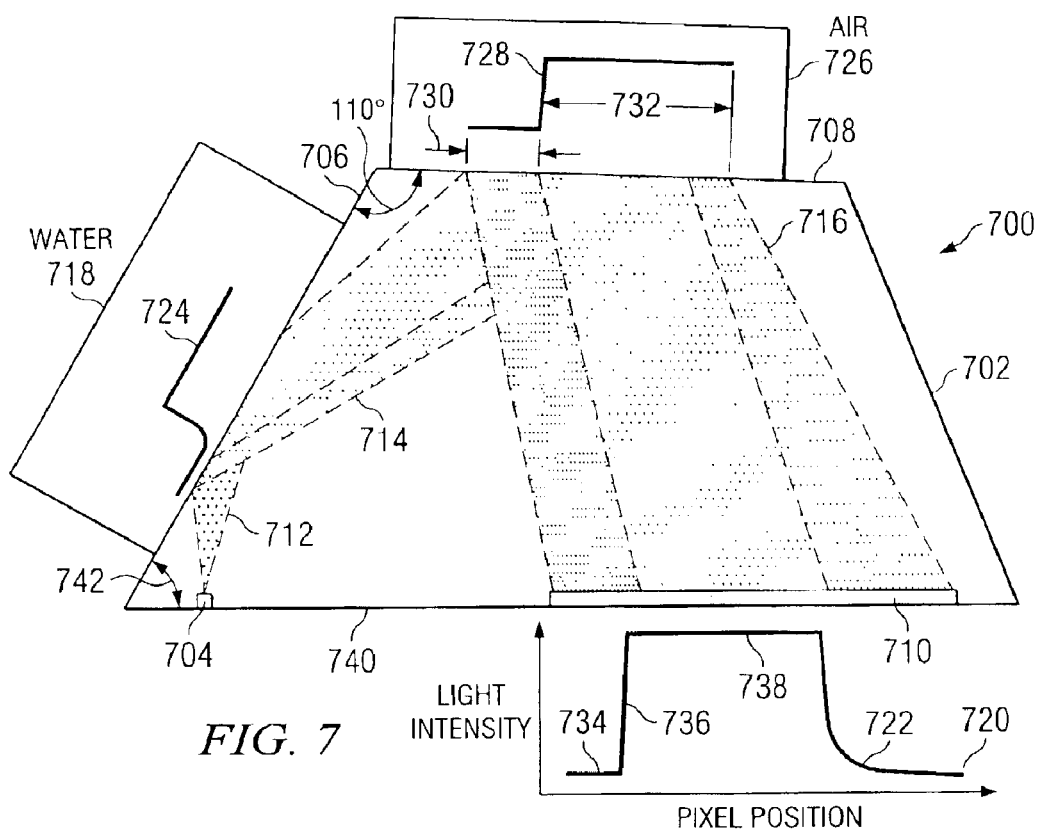
FIG. 7 shows a calibration technique for a critical angle sensor according the principles of the present invention.
Figure 8:
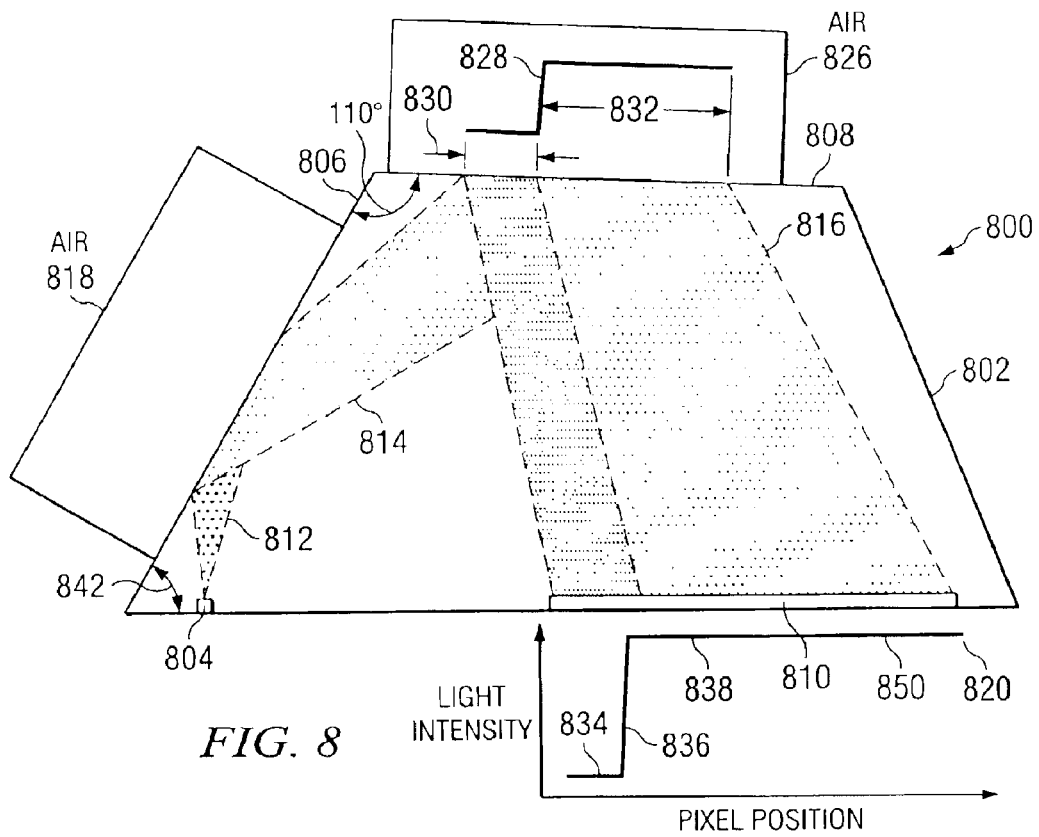
FIG. 8 shows the calibration technique of FIG. 7 without water present on the sensing surface.

A critical angle sensor employing the principles of the present invention is shown in FIG. 7 generally as 700. This sensor is similar to the sensor 300 shown in FIG. 3 and similar components have similar reference numerals. The sensor comprises a housing 702 having a bottom 740 on which a light source 704 which emits a beam of light 712 is located. The housing is formed from a material transparent to the light from light source 704. The light 712 impinges upon sensing surface 706 which is an optically flat surface but does not have a surface plasmon resonance element thereon. As shown in FIG. 7, water 718 is present on sensing surface 706 and has a characteristic 724, as shown in FIG. 3. The housing 702 has a higher refractive index than that of water so that light is reflected at the interface 706 between the body 702 and water 718 to form a beam 714 in which impinges upon the top surface 708. The top surface 708 forms an angle of 110 degrees with respect to the sensing surface 706 and may not be parallel with the base 740. Unlike the sensor 300 shown in FIG. 3, the top surface 708 of the sensor 700 does not contain a mirror to reflect the light back down upon the photodetector 710. The top surface 708 is exposed to air. Light impinging upon the portion 730 of surface 708 at an angle less than the critical angle will pass through the surface 708 and into the air and be lost, although a very small amount of light will be reflected onto the photodetector. Light impinging upon the portion 732 of surface 708 which is equal to or greater than the critical angle will be reflected by total internal reflection and reflected to form a beam 716 which impinges upon photodetector 710. This characteristic 728 for the air 726 is shown above the surface 708 in FIG. 6. Below the photodetector 710 is a graph showing the light intensity that appears on photodetector 710 as a function of pixel position. The curve 720 has a first portion 734 which is essentially at zero or close to zero followed by a sharply rising portion 763 followed by a flat portion 738 and a decreasing portion 722 which is the characteristic 724 of the water 718, reversed due to the reflection by surface 708. In the absence of the water 718, the output curve will consist of portion 734, 736, 738 and a continued horizontal portion. This is shown in FIG. 8 in which all of the elements except 818 are identical to FIG. 7. Element 818 is air whereas element 718 is water. As can be seen from the graph, the TIR signature of air 834, 836, 838, which corresponds to the segments 734, 736, 738 is still present. The segment 850 remains essentially horizontal because of the absence of the pattern for water. Thus, with the water omitted, the TIR signature 734, 736, 738 will still be present and can still be utilized to calibrate the sensor. Although the shapes of the curves 602, 604 will be different, the same principle illustrated with respect to FIG. 6 can be utilized to calibrate the sensor of FIG. 7.

As illustrated the angle between the sensing surface 706 and the top surface 708 is 110 degrees, as with the embodiment shown in FIG. 4. The angle 742 between the sensing surface and sensing surface 706 and the bottom 740 will be 50 degrees to detect water on the sensing surface or 60 degrees to detect oil on the sensing surface 706.

While the invention has been particularly shown and described with reference to preferred embodiments thereof, it is well understood by those skilled in the art as various changes and modifications can be made in the invention without departing form the spirit and scope of the invention as defined by the appended claims. For example, the materials chosen for the housing and the angles between the surface thereof can be modified to meet the requirements of a particular design, as is well know to those skilled in the art.

What is claimed is:

1. In a surface plasmon resonance sensor or critical angle sensor having a housing containing a light source and a photodetector, the housing having a sensing surface having altered optical properties when in contact with a sample and a reflecting surface for directing light within the housing so that light from the light source is reflected by the sensing surface and the reflecting surface onto the photodetector, a self contained calibration standard wherein the reflector surface comprises an optically flat surface on the housing having no reflective material thereon and having an outside of the flat surface exposed to air and wherein the housing is made of a light transmissive material for light from the light source having a higher index of refraction than air, light impinging on the flat surface having an angle of incidence which is equal to or greater than a critical angle being reflected to a path which impinges onto the photodetector, whereby a characteristic response is detected by the photodetector which is indicative of a calibration point.

2. The sensor of claim 1 wherein the sensor is surface plasmon resonance sensor having a thin surface plasmon resonance layer, the surface plasmon resonance layer having an interior surface disposed on the sensing surface and an outer surface, the surface plasmon resonance layer and the photodetector being disposed relative to each other so that radiation from the light source is reflected off the interior surface and strikes the photodetector, whereby the intensity of light reflected onto the photodetector varies with position along the photodetector, the intensity variation being affected by material on the exterior of the surface plasmon resonance layer.

3. The sensor of claim 2 wherein the refractive index of the material on the exterior of the surface plasmon resonance layer changes the angle of incidence of polarized light at which resonance occurs.

4. The sensor of claim 3 wherein the intensity of light reflected from the interior surface of the surface plasmon resonance layer is diminished at the angle of incidence at which resonance occurs.

5. The sensor of claim 2 wherein the housing, the source and the photodetector are integrally formed.

6. The sensor of claim 5 wherein the light source and photodetector are formed on a circuit board which is attached to one surface of the housing.

7. The sensor of claim 2 wherein the reflecting surface is formed by polishing a molded surface so that it is optically flat.

8. The sensor of claim 2 wherein the reflecting surface is a glass plate attached to a molded surface, space between the plate and the reflecting surface being filled with a material having substantially the same index of refraction as the housing.

9. The sensor of claim 1 wherein the sensor is a critical angle sensor having a unitary housing integrally encapsulating the light source and the photodetector, a portion of the light emitted by the light source being reflected off an interface between the sensing surface and the sample of interest, the photodetector being calibrated to determine the relative intensity of light reflected with respect to the amount of light emitted.

10. The sensor of claim 9 wherein the light source and the photodetector are mounted on one surface of a platform, the unitary housing being coupled to the platform.

11. The sensor of claim 9 wherein the reflecting surface is formed by polishing a molded surface so that it is optically flat.

12. The sensor of claim 9 wherein the reflecting surface is a glass plate attached to a molded surface, space between the plate and the reflecting surface being filled with a material having substantially the same index of refraction as the housing.

13. A surface plasmon sensor or critical angle sensor comprising:

a light transmissive housing having a higher index of refraction than air;

a light source disposed within the housing;

a photodetector disposed within the housing;

a sensing surface formed on one side of the housing;

a reflecting surface formed on another side of the housing having an exterior of the surface exposed to air, wherein there is no reflecting material on the reflecting surface, the light source, photodetector, sensing surface and reflecting surface being disposed in a light path wherein light emitted by the light source which impinges on the reflecting surface at an angle equal to or greater than a critical angle is reflected by the reflecting surface to a path in which it impinges on the photodetector and wherein light emitted by the light source which impinges on the reflecting surface at an angle less than the critical angle is refracted into the air, whereby the air-backed reflector surface generates a total internal reflection signature for calibrating the sensor.

14. The sensor of claim 13 wherein the sensor is surface plasmon resonance sensor having a thin surface plasmon resonance layer, the surface plasmon layer having an interior surface disposed on the sensing surface and an outer surface, the surface plasmon resonance layer and the photodetector being disposed relative to each other so that radiation from the light source is reflected off the interior surface and strikes the photodetector, whereby the intensity of light reflected onto the photodetector varies with position along the photodetector, the intensity variation being affected by material on the exterior of the surface plasmon resonance layer.

15. The sensor of claim 13 wherein the refractive index of the material on the exterior of the surface plasmon resonance layer changes the angle of incidence of polarized light at which resonance occurs.

16. The sensor of claim 15 wherein the intensity of light reflected from the interior surface of the surface plasmon resonance layer is diminished at the angle of incidence at which resonance occurs.

17. The sensor of claim 13 wherein the housing, the source and the photodetector are integrally formed.

18. The sensor of claim 13 wherein the light source and photodetector are formed on a circuit board which is attached to one surface of the housing.

19. A method of calibrating a surface plasmon sensor or critical angle sensor having a light source, sensing surface, reflecting surface having no reflective material thereon, having an exterior which is exposed to air, and photodetector enclosed in a light transmissive housing comprising:

exciting the light source;

detecting a signal generated in the photodetector by light from the light source;

finding a characteristic signature in the signal generated by the photodetector which is generated by total internal reflection at the reflecting surface;

calibrating the sensor response by utilizing the location of the characteristic signature on the photodetector.

20. The method of claim 19 wherein the calibration of the sensor response includes translating the response curve of the sensor along an axis depicting a position of elements of the photodetector.

* * * * *